United States Patent [19]

Smiley et al.

[11] Patent Number: 4,511,330
[45] Date of Patent: Apr. 16, 1985

[54] INTEGRATED ORAL MAGNETIC OSTEOGENIC APPLIANCES

[75] Inventors: Harry Smiley, White Plains; Abraham Blechman, Tappan, both of N.Y.

[73] Assignee: Medical Magnetics, Inc., Ramsey, N.J.

[21] Appl. No.: 538,380

[22] Filed: Oct. 3, 1983

Related U.S. Application Data

[63] Continuation-in-part of Ser. No. 322,423, Nov. 18, 1981, Pat. No. 4,424,030, which is a continuation of Ser. No. 19,427, Mar. 12, 1979, abandoned.

[51] Int. Cl.³ .................................................. A61C 7/00
[52] U.S. Cl. .................................................. 433/18
[58] Field of Search .................... 433/189; 128/419 F, 128/1.3, 82.1

[56] References Cited

U.S. PATENT DOCUMENTS

| 427,468 | 5/1890 | Dow | 128/82.1 |
|---|---|---|---|
| 3,353,271 | 11/1967 | Blechman | 433/18 |
| 4,076,022 | 2/1978 | Walker | 128/82.1 |
| 4,266,533 | 5/1981 | Ryaby et al. | 128/419 |

Primary Examiner—Robert Peshock
Attorney, Agent, or Firm—Roy C. Hopgood

[57] ABSTRACT

The invention contemplates a body-mounted fixture for supporting a source of magnetic flux in position as appropriate to coact with intra-oral magnet structure, to non-invasively achieve orthodontic and/or periodontic therapy. In coaction with an intra-oral magnet, the extra-orally mounted source of magnetic flux establishes an orthodontic-force environment (with a range of resultant-force magnitudes and directions), and/or a therapeutically beneficial environment for a selected region of tooth and alveolar bone requiring osteogenesis and soft-tissue repair.

20 Claims, 7 Drawing Figures

INTEGRATED ORAL MAGNETIC OSTEOGENIC APPLIANCES

BACKGROUND OF THE INVENTION

This application is a continuation-in-part of our copending application Ser. No. 322,423, filed Nov. 18, 1981 and now U.S. Pat. No. 4,424,030 issued Jan. 3, 1984, and said copending application is a continuation of our original application, Ser. No. 019,427, filed Mar. 12, 1979 (now abandoned).

Said applications disclose various embodiments of magnetic osteogenic and orthodontic appliances, in which relative movement of magnetic devices produces varying currents in localized regions in aid of soft-tissue repair and osteogenesis. Some of the disclosed arrangements utilize magnetic devices for essentially only orthodontic purposes, while others are primarily adapted for soft-tissue repair and osteogenesis. Among the disclosed arrangements is one in which an extra-oral magnet carried by headgear worn by the patient is adapted to cooperate with an intra-oral magnetic module mounted to and forming part of an orthodontic appliance. In that arrangement, there is no physical contact between the extra-oral and intra-oral magnets, and magnetic-force fields are generated through the cheek without sensation to the patient. The extra-oral magnet can be mounted to produce high, medium, or low pulling forces, as required, and patient cooperation is required.

BRIEF STATEMENT OF THE INVENTION

It is an object of the invention to provide means whereby an extra-oral source of magnetic flux may be positioned for magnetic coaction with one or more intra-oral magnets, in aid of orthodontic and/or periodontal therapy, including alveolar-ridge maintenance in edentulous patients.

Another object is to meet the above object with apparatus whereby a region of alveolar bone requiring osteogenesis and/or soft-tissue repair may be exposed to therapeutically beneficial varying magnetic fields, without requiring a power source within the body.

It is also an object to provide improved means for subjecting a localized region of tooth and/or alveolar bone and/or tissue to a therapeutically beneficial non-varying magnetic field, with or without selective-variation of the magnetic field.

Still another object is to achieve the above objects with non-invasive structure having fixed or removable, self-retaining positioning support for one or more intra-oral magnets within the mouth, and with mechanically independent removable, self-retaining positioning support for one or more extra-oral magnet devices external to the mouth.

The invention achieves the above objects in a fixture comprising headgear means adapted to conform to and be worn by the patient. The headgear means includes a mounting portion configured to retain magnetic means in a selected position and orientation adjacent a region of one cheek, the region being local and proximate to the buccal side of maxillary or mandible teeth, as the case may be. The mounting and orientation are selected for desired coaction with intra-orally mounted magnetic means, to establish a varying and/or non-varying magnetic-field environment in aid of periodontic and/or orthodontic therapy.

DETAILED DESCRIPTION

The invention will be illustratively described for several embodiments and applications, in conjunction with the accompanying drawings, in which.

Figure 1:
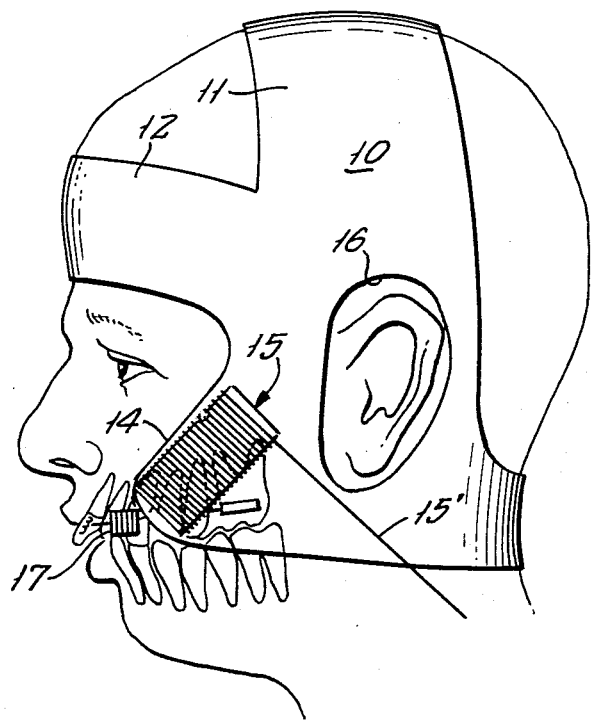
FIG. 1 is a left lateral view of extra-orally mounted magnetic structure operating with intra-orally mounted magnet structure forming part of an orthodontic or periodontic appliance.

In FIG. 1, the invention is shown in application to a headgear fixture 10 having top, front and rear strap-like portions 11-12-13 adapted to head contours such that vertically suspended and front/rear stability is provided for a mounting portion 14 for magnetic means 15, ear cut-outs being provided, as at 16. The mounting portion 14 is in substantial overlap with the buccal side of maxillary and/or mandible teeth, and it is adjacent the involved cheek. As shown, the extra-orally mounted magnetic means 15 is poised for orthodontic coaction with an intra-oral magnet module 17, which is shown to be archwire-mounted in the manner described in greater detail in said copending application Ser. No. 322,423. There is thus no physical contact between the extra-oral magnet structure 15 and the intra-oral magnetic module 17, and magnetic force fields are generated through the cheek without sensation to the patient. It suffices to note that intra-oral module 17 includes a permanent magnet which is permanently polarized in the direction locally along the archwire, and that the extra-oral magentic means includes an elongate core of flux-conducting material which may be permanently polarized along an axis which is locally substantially parallel to the involved cheek, adjacent end poles of the intra-oral module 17 and of the extra-oral structure 15; the magnet means 15-17 are shown close to but short of overlap, as viewed in the aspect of FIG. 1, it being understood that these adjacent poles are also laterally offset, to substantially the local thickness of the cheek. The orientation shown for the extra-orally mounted structure is upwardly inclined from the adjacent-poles region, and therefore orthodontically operative intra-oral force developed by opposite polarities at the poles in the adjacent-poles region will be characterized by orally distal, upward and laterally outward components.

Although the core of magnetic structure 15 may be permanently magnetized, it is shown with a multi-turn excitation coil linked thereto, to establish flux development along the described elongation axis of magnetic-flux development; one of two flexible leads to the excitation coil of means 15 is shown at 15', and the other is omitted, for better clarity in the drawing.

It will be understood that the orthodontic "pull" derived from opposite adjacent poles of the intra-oral and extra-oral magnets will be a function of materials (preferably SmCo for any permanent magnet), adjacent-pole spacing, and/or strength of coil excitation in the extra-oral magnetic means 15. If such excitation is primarily d-c, then the orthodontic "pull" is the principal result, although small transient cycles of lateral displacement of means 15 may accompany jaw actuation, with concomitant changes in the spacing between the coacting adjacent poles. Such changes are necessarily the cause of varying magnetic-field strengths in the space between the adjacent poles, giving rise to therapeutic benefits induced in affected tissues and cells within the varying field. It will be understood that, beyond the high, medium or low "pull" forces that result from corresponding levels of coil excitation, a varying excitation of the coil will develop a correspondingly varying magnetic field, with therapeutically beneficial consequence within the affected body region.

Figure 2:
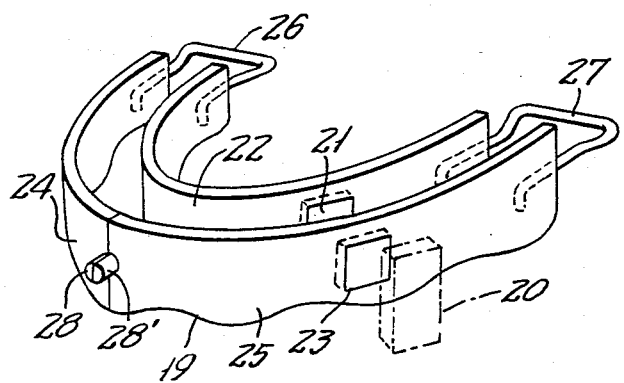
FIG. 2 is a simplified view in perspective to illustrate mandible-referenced intra-oral magnet-mounting structure for coaction with extra-orally mounted magnetic-means.
Figure 3:
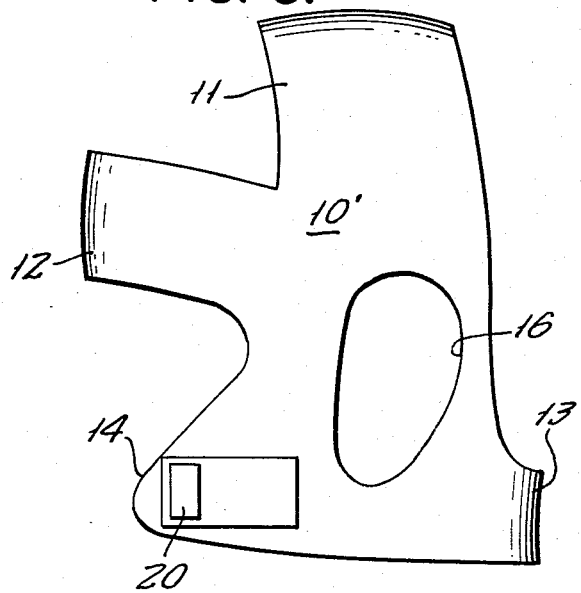
FIG. 3 is a view in side elevation, to show provision for extra-oral mounting of magnetic means to coact with the intra-oral magnetic means of FIG. 2.

FIGS. 2 and 3 illustrate structure utilizing a headgear fixture 10' of the nature described for FIG. 1 but mounting a permanently magnetized extra-oral element 20 for such coaction with intra-oral magnet structure as to primarily establish a varying magnetic-field environment in aid of osteogenesis and soft-tissue repair in a given local region of one or more mandible teeth and associated alveolar bone.

Figure 2A:
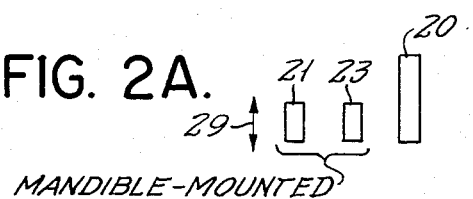
FIG. 2A is a schematic diagram in aid of describing magnet coaction for the arrangement of FIG. 2.

The intra-oral fixture of FIG. 2 is one of those described in our copending application Ser. No. 538,491, now U.S. Pat. No. 4,484,895, issued 11/27/84, filed on even date herewith, and therefore reference is made to said application for discussion thereof. It suffices here to identify a first or lingual permanent magnet 21 mounted to an arcuate flange or wall 22, which is conformed to the lingual side of the course of the mandibular arch, and a second permanent magnet 23 mounted to one of two removably connectable buccal flange or wall members 24–25 which are conformed to the buccal side of said course; the corresponding distal ends of members 24–22 are compliantly connected by a wire 26, and the distal ends of members 25–22 are compliantly connected by a wire 27, while the abutting front ends of members 24–25 are removably connected at 28–25' by elastic means (not shown). The magnets 20-21-23 are all polarized in the direction through the cheek and affected tooth and bone, and their polarization directions are preferably flux-aiding; illustratively therefore, the south pole of magnet 21 faces the north pole of magnet 23, and the south pole of magnet 23 faces the north pole of magnet 20. Preferably also, since mandible-mounted magnets 21–23 will move (upon jaw articulation) with respect to the maxilla, and since the extra-oral magnet is necessarily relatively fixed with respect to the maxilla, the extra-oral magnet 20 is vertically positioned (1) to have maximum laterally projected overlap with magnet 23 when the jaws are fully closed and (2) to quickly reduce the magnitude of flux-aiding coaction for any jaw movement away from the fully closed condition. This relation for the fully closed jaws is schematically suggested in FIG. 2A, where mandibular displacement is suggested by a double-headed arrow 29.

Figure 4:
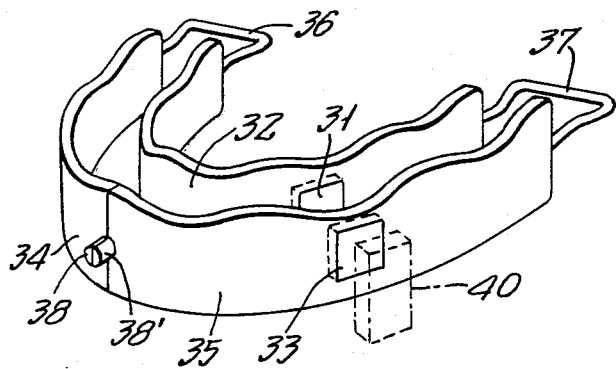
FIG. 4 is a view similar to FIG. 2, to illustrate a maxillary-based mounting of intra-oral magnetic means.

The intra-oral fixture of FIG. 4 is similar to that of FIG. 2, except that it is inverted, for maxilla tooth and bone conformance and retention. Thus, in FIG. 4 a first or lingual permanent magnet 31 is carried by an arcuate lingual wall member 32, and a second or buccal permanent magnet 33 is carried by one of two separably connected buccal wall members 34–35, corresponding distal wall ends being compliantly connected by means 36–37.

Figure 4A:
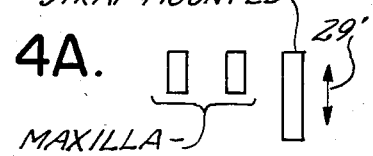
FIG. 4A is a view similar to FIG. 2, but applicable to the maxillary-based intra-oral situation of FIG. 4.
Figure 5:
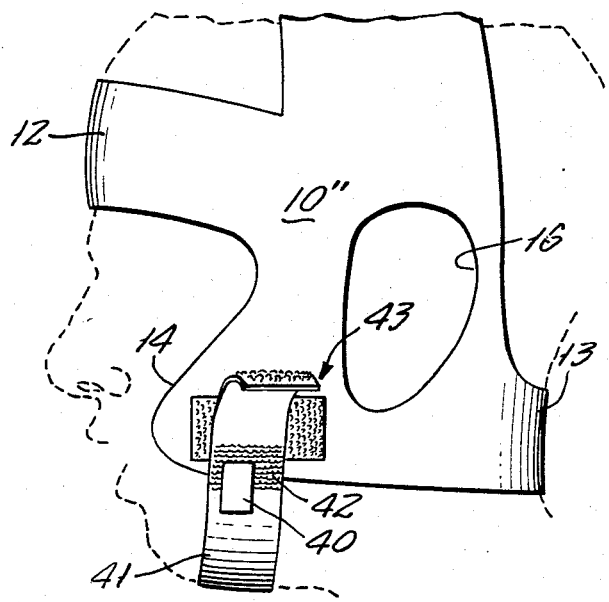
FIG. 5 is a view similar to FIG. 3, but applicable to the maxillary-based intra-oral situation of FIG. 4.

The extra-oral fixture or headgear 10" of FIG. 5 serves to position an extra-oral magnet 40 for coaction with intra-oral magnets 31-33, in much the same manner as indicated for extra-oral magnet 20 in relation to intra-oral magnets 21-23 in FIG. 2. The difference in the case of FIGS. 4 and 5, however, is that the intra-oral magnets 31-33, being maxilla-mounted, are relatively fixed, and jaw-actuated relative motion between intra-oral and extra-oral magnetic fields relies upon the extra-oral magnet being effectively mandible-mounted. In the form shown in FIG. 5, this result is achieved by providing headgear 10" of FIG. 5 with a removable chin strap 41 to which magnet 40 is mounted, and by providing elastic means 42 in the removable connection of strap 41 to the headgear region 14, a Velcro-type hook-and-loop provision being indicated at 43 for this purpose. The schematic diagram of FIG. 4A adopts the style of FIG. 2A to bring out the difference between action and relative positioning in the FIG. 4/5 arrangement as compared to the FIG. 2/3 arrangement; and, as with FIG. 2A, the relative elevation of the magnets of FIG. 4A will be understood to reflect the jaw-closed relation.

The described embodiments of the invention will be seen to achieve the stated objects. Headgear fixtures as described afford the dental practioner not only an extended dimension of magnet mountability for coaction with intra-oral magnet structures, for non-invasive orthodontic and/or periodontic purposes, but such an extra-oral fixture also enables the intra-orally effective application of stronger magnetic fields which may be of steady-state mode, controllably-variable mode, or combinations of the two modes.

Although both lingual and buccal magnets have been shown and described, for coaction with extra-oral magnet structure, it will be understood that use of both intra-oral magnets is not necessarily required. For example, the mere provision of a lingual magnet 21 (31) is enough to establish therapeutically beneficial flux development in the tooth and bone region exposed thereto.

Also, the intra-oral magnets may be mounted to such other means within the mouth as may be compatible with magnetic coaction and reaction described above. Thus a conventional dental plate may be a fixture to which one or more intra-oral magnets are mounted. And in embodiments as shown in FIGS. 2 and 4, it will be understood that custom-fit of the intra-oral positioning fixture includes appropriate undulated contouring of the base profile, as by scissors-cut of the skirt 19 of buccal flange 25 in FIG. 2, to provide maximum overlap with the alevolar ridge, without chafing contact with the gums.

Various permanent-magnet materials are discussed in said copending application Ser. No. 322,423 and therefore their discussion need not be repeated. We merely state our present preference for SmCo as the magnet material and indicate our preference that each such magnet be protectively coated with bio-compatible material, such as an acrylic.

It may be said of either or both of the embodiments of FIGS. 2 and 5 that they permit of so positioning the intra-oral and extra-oral magnets with respect to each other that the greatest change of magnetic flux will occur in the affected region of treatment, at or near the jaw-closed condition, thus effecting the greatest coupling to tissues and/or cells, and thus also having the maximum osteogenic effect at the same time that orthodontic correction force is at maximum.

While the invention has been described in detail for illustrative embodiments, it will be understood that modification may be made without departing from the scope of the invention. For example, the showings in FIGS. 2 and 4 for lingual magnetic elements at 21 and 31 will be understood to be schematic and to include such movably mounted and tongue-actuable embodiments as are more fully discussed in our said copending application filed on even date herewith.

Further, by way of example, although usage of plural magnets has been described in the context of all such magnets being permanently polarized, it is not necessary that they all be polarized to achieve a beneficial orthodontic or osteogenic or periodontic result. For orthodontic purposes, it is sufficient that one permanent magnet or other source of magnetic flux be established and that one or more elements of magnetic-flux conducting material serve for attractive coaction therewith. And for an osteogenic or periodontic result, it is again sufficient to employ a single source of magnetic flux, for magnetic-field variation as a function of relative movement between one of the elements as the source and the other (or another) of the elements as a means of parasitic coaction with the source element. Thus, reference herein to plural polarized magnet elements reacting with each other merely states a preferred relationship, and non-polarized parasitic reaction of the character indicated is included within the compass of the invention.

It is also be be understood that the expression "non-invasive" as used herein applies to the fact that magnetic fields and changing magnetic fields, as the same are exposed to tooth, bone and other body tissue, are surgically non-invasively applied. The expression "non-invasive" as used herein thus does not preclude applicability of magnetic fields of the invention to tooth, bone or other body tissue which may have been surgically implanted, as for reasons of bone grafting or other reinforcement.

What is claimed is:

1. In combination for use in orthodontic and/or periodontal therapy, an extra-oral positioning fixture comprising headgear means having top, front and rear strap-like portions adapted to conform to and be retained by the head of a patient, said headgear means including a mounting portion configured to retain its position adjacent a region of one cheek and in substantial overlap with the buccal side of maxillary and/or mandible teeth; and magnetically coacting means including an intra-orally mounted element of magnetic flux-conducting material on the lingual side of a tooth near said region and a source of magnetic flux carried by said mounting means.

2. The combination of claim 21, in which said source is a permanent magnet.

3. The combination of claim 2, in which the polarization axis of said magnet is predominantly transverse to said region.

4. The combination of claim 2, in which the polarization axis of said magnet is predominantly parallel to the cheek in said region.

5. The combination of claim 21, in which said source comprises a core of magnetic-flux-conducting material extending between spaced poles thereof, and an electrical winding linked to said core.

6. The combination of claim 21, in which said headgear means comprises a skull-conforming body portion and a chin-strap portion having elastic connection to said body portion, and in which said mounting portion is on said chin-strap portion.

7. The combination of claim 1, in which said intra-orally mounted element is permanently magnetized.

8. The combination of claim 1, in which said intra-orally mounted element is one of two, the second of said two being on the buccal side of a tooth near said region.

9. The combination of claim 8, in which said elements are permanent magnets and are respectively mounted with their polarization axes in substantially the same direction through said region.

10. The combination of claim 7, in which the intra-orally mounted magnetized element is orthodontically fixed to at least one tooth, and in which said extra-orally mounted source of magnetic flux is oriented for orthodontically directional magnetic-force coaction with said intra-orally mounted element.

11. The combination of claim 10, in which the orientation of said extra-orally mounted source establishes a flux field on a directional axis that is predominantly parallel to the cheek in said region.

12. The combination of claim 7, in which the intra-orally mounted magnetized element is mandible-mounted.

13. The combination of claim 7, in which the intra-orally mounted magnetized element is maxilla-mounted.

14. The combination of claim 1, in which said headgear means comprises a skull-conforming body portion and a chin-strap portion having elastic connection to said body portion, and in which said mounting portion is on said chin-strap portion.

15. In combination, headgear means having strap-like portions adapted to conform to and be retained by the head of a patient, at least one intra-orally mounted permanent magnet establishing a field of polarized magnetic-flux development in a region of alveolar bone requiring maintenance and/or repair, said headgear means including mounting structure in external adjacency to said region, and at least one extra-orally permanent magnet carried by said mounting structure and establishing a field of polarized magnetic-flux development in magnetic coaction with or reaction to the field of said intra-orally mounted magnet.

16. The combination of claim 15, in which the mounting structure for the extra-oral magnet includes a first portion movable in response to maxillary movement and a second portion which is relatively immobile in response to maxillary movement, said intra-orally mounted magnet being mandible-mounted and said extra-orally mounted magnet being mounted to said second portion and therefore maxillary-referenced.

17. The combination of claim 15, in which the mounting structure for the extra-oral magnet includes a first portion movable in response to maxillary movement and a second portion which is relatively immobile in response to maxillary movement, said intra-orally mounted magnet being maxillary-mounted, and said extra-orally mounted magnet being mounted to said second portion and therefor maxillary-referenced.

18. The combination of claim 15, in which the mounting structure for the extra-oral magnet includes a first portion movable in response to maxillary movement and a second portion which is relatively immobile in response to maxillary movement, said intra-orally mounted magnet being maxillary-mounted, and said extra-orally mounted magnet being mounted to said one portion and therefore mandible-referenced.

19. In combination, headgear means having strap-like portions adapted to conform to and be retained by the head of a patient, at least one intra-orally mounted element of magnetic-flux-conducting material in a region of alveolar bone requiring maintenance and/or repair, said headgear means including mounting structure in external adjacency to said region, and at least one extra-orally mounted permanent magnet carried by said mounting structure, said intra-oral and extra-oral elements being positioned for magnetic coaction of or magnetic reaction by said intra-oral-element with respect to the magnetic field of said extra-orally mounted magnet.

20. The combination of claim 19, in which said intra-oral element is movable in response to tongue actuation.

* * * * *